(12) United States Patent
Highsmith et al.

(10) Patent No.: US 7,332,457 B2
(45) Date of Patent: Feb. 19, 2008

(54) AGRICULTURAL CHEMICAL SUSPENSIONS

(75) Inventors: Ronald E. Highsmith, Chesterfield, VA (US); Robert A. Foster, Richmond, VA (US)

(73) Assignee: Honeywell International Inc., Morristown, NJ (US)

( * ) Notice: Subject to any disclaimer, the term of this patent is extended or adjusted under 35 U.S.C. 154(b) by 769 days.

(21) Appl. No.: 09/886,700

(22) Filed: Jun. 21, 2001

(65) Prior Publication Data
US 2002/0065198 A1 May 30, 2002

Related U.S. Application Data

(60) Provisional application No. 60/233,457, filed on Sep. 18, 2000.

(51) Int. Cl.
*A01N 25/00* (2006.01)
*A01N 63/00* (2006.01)
*A01N 59/02* (2006.01)
*C05C 3/00* (2006.01)

(52) U.S. Cl. .................. 504/116.1; 504/118; 504/188
(58) Field of Classification Search ........... 504/206, 504/142, 118, 116.1, 188; 71/61
See application file for complete search history.

(56) References Cited

U.S. PATENT DOCUMENTS

| | | | | |
|---|---|---|---|---|
| 3,317,635 | A | 5/1967 | Osmond et al. ............ 260/881 |
| 3,793,015 | A | 2/1974 | Van Engeland et al. .... 430/112 |
| 3,817,727 | A | 6/1974 | Yancey ........................ 51/298 |
| 4,372,777 | A * | 2/1983 | LeClair et al. ................ 71/93 |
| 4,393,151 | A | 7/1983 | Dawans et al. ............ 523/130 |
| 4,526,606 | A | 7/1985 | Formaini |
| 5,221,319 | A * | 6/1993 | Van Haften et al. ....... 504/144 |
| 5,612,285 | A * | 3/1997 | Arnold ....................... 504/206 |
| 5,707,551 | A | 1/1998 | Pallas et al. ............... 252/308 |
| 5,906,962 | A | 5/1999 | Pallas et al. ............... 504/116 |
| 6,083,875 | A * | 7/2000 | Sato et al. ................. 504/127 |

FOREIGN PATENT DOCUMENTS

| | | |
|---|---|---|
| DE | 2312372 | 9/1973 |
| EP | 253682 | 1/1988 |
| GB | 1151141 | 5/1969 |
| JP | 63303903 | * 12/1988 |
| JP | 02104502 | 4/1990 |
| JP | 05105606 | 4/1993 |

OTHER PUBLICATIONS

Roberts et al, Basic Principles of Organic Chemistry, 2nd edition, W. A. Benjamin, Inc., 1977 and 1964.*
Y. Yan et al., "Rheology of Oil-in Water Emulsions with Added Solids", Chem. Eng. Sci, 46 (4), 985-994 (19910.
R.M. Turian, "Characterization, settling, and rheology of concentrate fine particulate mineral slurries", Powder Technology, 93, 219-223 (1997).

* cited by examiner

Primary Examiner—Alton Pryor
(74) Attorney, Agent, or Firm—Bruce Bradford

(57) ABSTRACT

Stable concentrated suspensions readily dispersible in water comprising one or more agricultural solids, a single non-ionic surfactant and a water-soluble glycol liquid. The agricultural solids include fertilizers, adjuvants, herbicides, pesticides and combinations thereof approved for use with foods. The non-ionic surfactant is an alkyl-phenoxy-poly (ethylenoxide)alkanol, an ethoxylated aliphatic $C_{11}$ to $C_{15}$ alcohol, an ethylene oxide-propylene oxide block copolymer or an ethoxylated fatty acid. Preferably, the surfactant has an average molecular weight from about 300 to about 1000. The water-soluble glycol liquid is ethylene glycol, propylene glycol, or mixtures thereof. The agricultural solid particles are at least about 99 wt. % passable through a Tyler #48 sieve. The suspensions of the invention exhibit physical stability during normal storage conditions, good pourability, and are readily dispersed in water.

20 Claims, 1 Drawing Sheet

AGRICULTURAL CHEMICAL SUSPENSIONS

CROSS-REFERENCES TO RELATED APPLICATIONS

This application claims the benefit of provisional application Ser. No. 60/233,457 filed Sep. 18,2000 and is related to co-pending application Ser. No. 09/855,481 filed May 15, 2001, 2001 entitled "Ammonium Sulfate Suspensions in Oils".

BACKGROUND OF THE INVENTION

1. Field of the Invention

The present invention relates to concentrated glycol suspensions of water-soluble agricultural materials having superior stability and pour properties, and that upon dilution in a suitable volume of water, are suitable for application to plants as herbicidal compositions, adjuvants in herbicidal compositions, or fertilizers, or that may be used for other purposes.

2. Description of the Related Art

When growing crops in a field, it is important to kill or control the growth of undesirable plants (weeds) in the field. If not controlled, the weeds compete with crop plants for essential resources such as soil nutrients, water and sunlight. By removing a fraction of the resources or otherwise reducing the availability of these resources to crop plants, the weeds restrict crop growth, resulting in loss of crop yield.

Timely and judicious use of herbicides can provide weed control to minimize crop losses and production costs. Herbicides such as glyphosate (N-phosphonomethyl glycine) and many others are useful for control of a large variety of weeds. When used in an herbicidal composition, glyphosate is generally in the form of one of its various salts in solution, preferably an aqueous solution.

Adjuvants are materials that enhance the action of herbicides by promoting adsorption and translocation and by complexing antagonistic metal ions in the water used to make the herbicide solution. Ammonium sulfate has been known as an adjuvant for several decades. It is perhaps the most important commercial adjuvant and is also widely used as a fertilizer.

Herbicides are typically applied to field crops by spraying an aqueous mixture of several components. Polymers that inhibit spray drift, defoamers, and other chemicals that enhance the performance of an herbicide are sometimes mixed with the ammonium sulfate. All components of a mixture are typically ground to a small particle size in order to reduce the time required to dissolve. Growers and contract applicators use a "mix" tank to prepare the herbicide mixture. A typical mix consists of about 800 pounds of water, 8 to 17 pounds of herbicide, and 8 to 17 pounds of dry adjuvant. The result is a 1% or 2% solution of herbicide and 1% or 2% of adjuvant. The typical tank has relatively poor mixing and the applicator, whether using a truck or airplane, usually has little time to wait for dissolution. Even small particles tend to fall to the bottom of the mix tank in clumps and are sometimes slow to dissolve. In addition, dry materials may generate undesirable dusty conditions, absorb moisture, tend to cake, and are difficult to meter.

Liquid preparations facilitate use. However, liquids may suffer disadvantages because of low product concentration. Agricultural materials of interest have limited water solubility. Freight, handling, and packaging costs can become a substantial part of the total product cost. As an example, the highest practical concentration of ammonium sulfate in aqueous solution is about 38%. This concentration drops to about 34% if drift retardant polymer is included. Water is the only practical solvent because ammonium sulfate is practically insoluble in all other common solvents. Thus, while aqueous solutions are not satisfactory, there remains a need for liquid agricultural products.

An alternative approach to a liquid product is to create a suspension. Many examples of aqueous suspensions of agricultural materials are known in the art. Japanese patents JP 05105606, JP 02104502, EP 253682, and U.S. Pat. No. 4,526,606 are exemplars. However, in aqueous suspensions of water-soluble materials, crystal dissolution and recrystallization occurs continually. This results in a progressive increase of the size of the particles and eventual setting. Therefore, it is desirable and convenient to be able to prepare high concentration suspensions of agricultural solids in liquids in which they are not appreciably soluble.

In order for solid materials, which are generally denser than liquids to remain suspended, they must be broken up into small particles. Generally, the smaller the particle the more stable the suspension. Colloidal particles of 0.001 mm (1 micron) or less in diameter form stable suspensions because of Brownian motion. However, the energy required to break down ammonium sulfate and most other materials to colloidal dimensions is extremely high and impractically costly.

The liquid in a suspension intended for agricultural purposes must comply with government regulations, and should be qualified for use with pesticides under the Code of Federal Regulations (C.F.R.). The liquid may be soluble or insoluble in water. Mineral oils and a few other oils such as soybean oil are approved for agricultural use under 40 C.F.R. 180.1001, paragraph c and have been used as adjuvants themselves. Petroleum distillates are also approved under this section of the C.F.R. provided they conform to the conditions of 21 C.F.R. 172.882 or 21 C.F.R. 172.884. Co-pending application Ser. No. 09/855.481 describes useful suspensions of agricultural materials in water-insoluble oils.

However, suspending liquids that are water-soluble may be advantageous in that they have the potential to facilitate dispersion and dissolution of suspended solids in the applicator's "mix" tank. Of importance to this invention, propylene glycol and dipropylene glycol are approved for agricultural use under paragraph c of 40 C.F.R. 180.1001, and ethylene glycol and diethylene glycol are approved under paragraph d of the same part.

It is not yet possible to predict what combination of liquid and solid will yield a stable suspension. There is little understanding of the fundamentals of suspensions. For instance, Yan et. al. state that. "the effect of particle size on the rheology of suspensions is a controversial subject" (Y. Yan, et. al., *Chem. Eng. Sci.*, 46(4), 985-994, (1991)). Other authors have claimed that the shape and ionic character of the particles can be important factors. For instance, R. M. Turian, et. al. in a paper published in *Powder Technology*, 93, 219-223 (1997) suggests that the "interparticle interaction effects were quite strong" for the suspensions he investigated. It is to be expected that different particles may present uniquely different properties.

Problems with use of agricultural suspensions may include syneresis, inability to pour, and difficulty dissolving. To begin with, suspensions must be stable. Syneresis is a phenomenon of phase separation marked by free clear liquid separating from a suspension. It is undesirable because it results in an inhomogeneous mixture. The most convenient method of measuring syneresis is to measure the depth of the free liquid in a container after sitting for some period of time compared to the total depth of the suspension and expressing the result in terms of percentage or fraction.

The first step in using an agricultural suspension is pouring it from its shipping container into a mix tank to be diluted for application. It is necessary that the suspension have the ability to be conveniently and quantitatively transferred from one container to another under the influence of gravity, i.e. to have good pourability. Pourability and suspension stability may be competitive properties. As previously noted, suspension stability generally increases as particle size decreases. However, suspension viscosity tends to increase as particle size becomes smaller. Suspension stability also generally increases with a higher viscosity suspending liquid. With some choices of particle size and suspending liquid the viscosity can become so high that the suspension will no longer pour. A balance between stability and pourability must be achieved.

The solids in a suspension must be readily dispersed and/or dissolved in a mix tank. If a suspension is too viscous or otherwise antagonistic toward water, the suspension will remain as large globules in the water and the suspended solids will be slow to dissolve. Dispersion means that the globules of the suspension break up into small liquid droplets to form a milky volume in the water. This is sometimes referred to as "bloom". The resulting high surface area allows the solid particles rapid access to water where they can dissolve quickly. Vigorous agitation can also result in good dispersion, but in mix tanks where agitation-is frequently marginal, the ability of a suspension to quickly and spontaneously "bloom" can significantly reduce dissolving times.

Suspensions are well known in the art although few have been reported that employ non-aqueous liquids. For instance, U.S. Pat. No. 3,793,015 and British Patent GB 1,151,141 reported stable suspensions of particles such as carbon black in aliphatic hydrocarbons using metal salts of pyrophosphates and similar agents as dispersing agents. The suspensions were described as useful in imaging such as xerography. U.S. Pat. No. 3,317,635 reported dispersions of polymer particles in organic liquids. These are different than conventional suspensions of solid materials since they are prepared by in situ polymerization of aqueous liquid droplets in a hydrocarbon fluid. U.S. Pat. No. 4,393,151 described suspensions of water-soluble polymers in a liquid hydrocarbon medium including a thickening agent. German Patent 2312372 described suspensions of polishing agents such as alumina, zirconia and silicon carbide in ethylene glycol thickened with a neutralized carboxymethylene resin. These suspension were not designed to be dispersible in water.

Surfactants and soluble polymers are often used to stabilize suspensions of particles. These may function by adsorption on the particle surface and may provide steric interference that inhibits settling. However, the interaction between a particular liquid, particle, and surfactant is impossible to predict.

Suspensions of water-soluble solids in non-aqueous water miscible fluids such as glycols, ketones, and alcohols are described in U.S. Pat. Nos. 5,707,551 and 5,906,962. Specific examples are suspensions of potassium nitrate and of ammonium dihydrogen phosphate in propylene glycol and diethylene glycol. Stability of the suspensions is obtained through use of a surfactant system having three necessary components and the possible inclusion of water. U.S. Pat. No. 5,906,962 describes a similar surfactant system additionally containing a water hydratable polysaccharide.

The first necessary component of U.S. Pat. No. 5,707,551 is a nonionic polymeric "viscosity improver", preferably a polymeric material with a volume mass of less than 15,000. The patent states that the "viscosity improver" increases viscosity. Most preferably, the "viscosity improvers" are ethylene-oxide-propylene oxide block copolymers having molecular weights between 1,122 and 15,000. Specific examples are the high molecular weight ethoxylated-propoxylated block copolymers ANTAROX® F-88 of 8,082 molecular weight, and ANTAROX® F-108 of 10,812 molecular weight. Among the possible "viscosity improvers" suggested by U.S. Pat. No. 5,707,551 are included the genera of ethoxylated alkyl phenols and ethoxylated aliphatic alcohols. No specific species of these genera are identified.

The second necessary component in U.S. Pat. No. 5,707,551 is an anionic surfactant whose functions are to control the viscosity increase caused by the first component and to adhere to the surface of the suspended solids.

The third necessary component is a bulky nonionic surfactant having a large hydrophobic substituent group. Such materials are known to provide steric interference that inhibits settling.

A fourth optional component in U.S. Pat. No. 5,707,551 is water. The water may be added to adjust the temperature coefficient of solubility of the suspended solids.

As noted above, U.S. Pat. No. 5,906,962 describes a similar surfactant system that includes yet an additional component consisting of a hydratable polysaccharide.

It is evident that the suspension systems described by U.S. Pat. Nos. 5,707,551 and 5,906,962 are complex, require much time and effort to adjust for each suspended solid, and are costly to manufacture and control. A need exists for a non-aqueous, water-soluble suspension system for agricultural solids that is simple, economic and easy to adjust for different suspended solids. In particular, a need exists for simple, low cost, stable, concentrated suspensions of ammonium sulfate that are readily dispersible in water and for other purposes.

SUMMARY OF THE INVENTION

The invention provides stable concentrated suspensions comprising agricultural solids, a single surfactant, and a water-soluble glycol liquid approved for agricultural application. An agricultural solid is a fertilizer, an adjuvant, a herbicide or a pesticide registered, or exempt from registration under 40 C.F.R. 180, "Tolerances and Exemptions From Tolerances For Pesticides in Food", Jul. 1, 2000.

In one embodiment, the invention provides stable concentrated suspensions comprising ammonium sulfate, a single surfactant and a water-soluble glycol liquid approved for agricultural application The surfactant is a non-ionic alkyl-phenoxy-poly(ethylenoxide)alkanol, an ethoxylated aliphatic $C_{11}$ to $C_{15}$ alcohol, an ethylene oxide-propylene oxide block copolymer or an ethoxylated fatty acid. Preferably, the surfactant has an average molecular weight from about 300 to about 1000. The water-soluble glycol liquid is ethylene glycol, propylene glycol, or mixtures thereof. The agricultural solid particles are at least about 99 wt. % passable through a Tyler #48 sieve The suspensions of the invention exhibit physical stability during normal storage conditions, good pourability, and are readily dispersed in water.

In another embodiment, the ammonium sulfate suspensions of the invention additionally contain methylthio-α-hyroxybutyric acid. It is surprisingly found that methylthio-α-hyroxybutyric acid enhances the stability and reduces the viscosity of the ammonium sulfate suspensions of the invention.

Suspensions of the invention containing ammonium sulfate, propylene glycol, and dodecylphenoxy poly(ethylene oxide) ethanol surfactant, diluted in water, and in combination with a herbicide, exhibit synergistic effects in killing difficult weeds. Herbicide manufacturers usually recommend applying double the dose of herbicide when difficult weeds are present. However, from an environmental point of view it is more desirable to use less herbicide and an adjuvant to obtain the same effect. The suspensions of the invention meet that need.

BRIEF DESCRIPTION OF THE DRAWINGS

In the accompanying drawing figures.

DETAILED DESCRIPTION OF THE INVENTION

Figure 1:
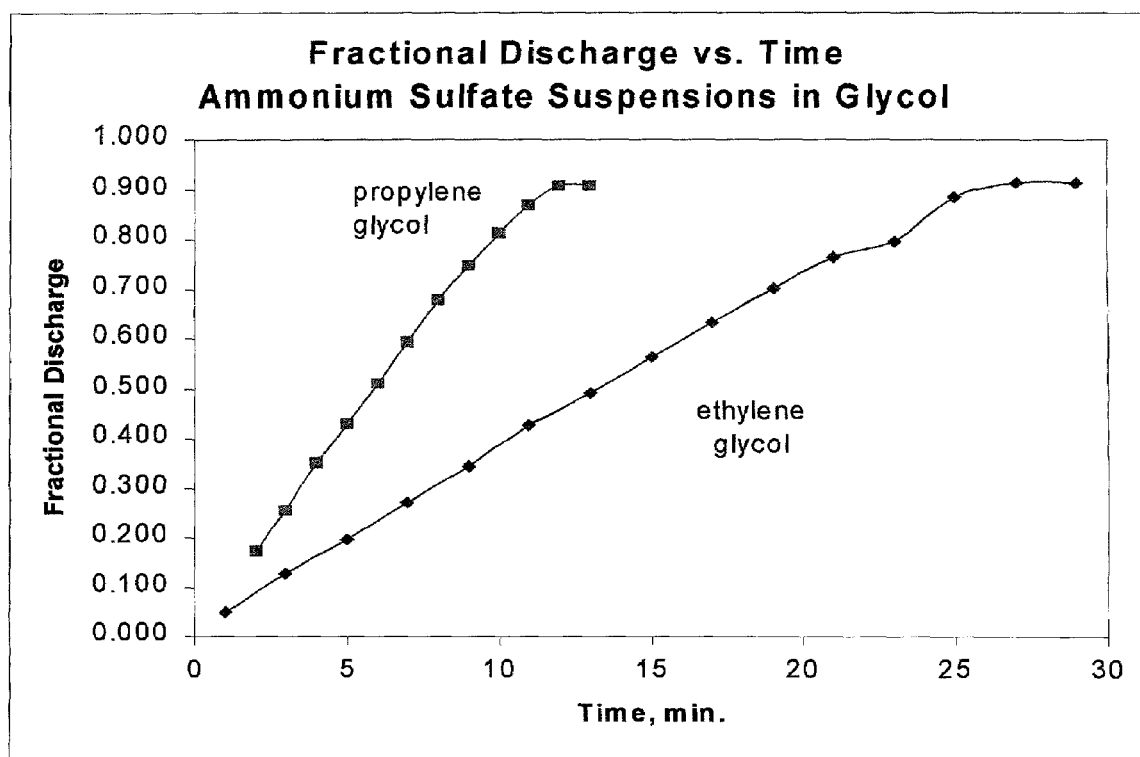
FIG. 1 shows plots of fractional discharge vs time for two suspensions of the invention.

The products of the invention are stable concentrated suspensions of agricultural solids readily dispersible in water. Preferably, the suspensions, upon dilution in a suitable volume of water, are suitable for application to plants as herbicidal compositions, adjuvants in herbicidal compositions, or fertilizers, or may be used for other purposes. For the purposes of this invention, an agricultural solid is a fertilizer, an adjuvant, a herbicide or a pesticide registered, or exempt from registration under 40 C.F.R. 180, "Tolerances and Exemptions From Tolerances For Pesticides in Food", Jul. 1, 2000.

The invention provides stable concentrated suspensions comprising agricultural solids, a single surfactant, and a water-soluble glycol liquid approved for agricultural application. More particularly, the invention provides stable concentrated suspensions comprising ammonium sulfate, a surfactant and a water-soluble glycol liquid approved for agricultural application.

An agricultural suspension of the invention is comprised of: agricultural solids consisting of at least one member selected from the group consisting of a fertilizer, an adjuvant, a herbicide and a pesticide, said agricultural solids having particles more than about 99 wt. % passable through a Tyler #48 sieve; a single non-ionic surfactant selected from the group consisting of alkyl-phenoxy-poly(ethylenoxide) alkanols, ethoxylated aliphatic $C_{11}$ to $C_{15}$ alcohols, ethylene oxide-propylene oxide block copolymers and ethoxylated fatty acids; and a water-soluble glycol liquid consisting of at least one member of the group consisting of ethylene glycol, and propylene glycol.

More particularly, the invention provides stable concentrated suspensions comprising ammonium sulfate particles more than about 99 wt. % passable through a Tyler #48 sieve; a single non-ionic surfactant selected from the group consisting of alkyl-phenoxy-poly(ethylenoxide)alkanol, ethoxylated aliphatic $C_{11}$ to $C_{15}$ alcohols, ethyleneoxide-propylene oxide block copolymers, and ethoxylated fatty acid; and a water-soluble glycol liquid consisting of at least one member of the group consisting of ethylene glycol, and propylene glycol.

In another embodiment, the ammonium sulfate suspensions of the invention additionally contain methylthio-α-hyroxybutyric acid.

The invention is based on the discovery that agricultural solids, having particles within a certain size range, and in a concentration range, in combination with a single surfactant can form stable suspensions in glycol liquids having both good stability and good pourability. This is a surprising result as the closest prior art system for suspending water-soluble solids in glycol liquids has no fewer than three required surfactants of different genera. The suspensions of the present invention are therefore much simpler to formulate and to produce, and are more economic than the suspensions of the prior art.

Generally any agricultural solid fertilizer, adjuvant, herbicide or pesticide or combination thereof having particles more than about 99 wt. % passable through a Tyler #48 sieve may be incorporated in a suspension of the invention. The concentration of the solid materials in the suspension should be between 20 wt. % and about 80%, and preferably between 50 and about 70%.

Preferred agricultural solids are ammonium sulfate $((NH_4)_2SO_4)$, diammonium phosphate $((NH_4)_2HPO_4)$ the isopropylamine salt of N-(phosphonomethyl) glycine and combinations thereof. The last named material is manufactured by Monsanto Co. and is sold under the name of RoundUp® DryPak. Ammonium sulfate is most preferred.

Generally, any ordinary ammonium sulfate that is commercially available and suitable for use as fertilizer may be used in the suspensions of this invention. One example of useful ammonium sulfate is commercially available from Honeywell International Inc. Preferably, the ammonium sulfate to be used in this invention is of at least about 95 wt % purity and contains less than about 0.2 wt % of water insoluble (filterable) organic or carbonaceous impurities. The filterable impurities are determined by dissolving 10 wt % of the ammonium sulfate in water at 23° C., then passing at least 50 g of the solution through a membrane filter of 0.45 micrometer opening size (e.g. Gelman Supor® brand filter). The organic and carbonaceous content as determined by combustion analysis of the dried filter cake should be less than about 0.2 wt % of the ammonium sulfate.

The particle size and particle size distribution of the ammonium sulfate are important to achieving the objectives of the invention. Generally, the smaller the particle the higher the viscosity and the better the stability of the suspensions. It is too costly to separate specific sizes of particles. It is desirable to be able to utilize the size distribution resulting from common grinding processes The suspensions of the invention have this advantage.

The ammonium sulfate particles used in the invention are substantially passable through a Tyler #48 sieve. It is preferred that at least 8 wt. % of the ammonium sulfate particles pass a Tyler #230 sieve. A most preferred particle size range for ammonium sulfate is as follows:

| Tyler Sieve No. | Opening Size, mm | Weight % Retained on Sieve |
|---|---|---|
| 48 | 0.30 | Less than 1 |
| 60 | 0.25 | 0-10 |
| 80 | 0.18 | 0-20 |
| 100 | 0.15 | 0-35 |
| 200 | 0.075 | 10-30 |
| 230 | 0.060 | 30-50 |

-continued

| Tyler Sieve No. | Opening Size, mm | Weight % Retained on Sieve |
| --- | --- | --- |
| 400 | 0.03 | 10-40 |
| pan | 0 | 10-20 |

This is representative of the size range produced by commercial ball milling of ammonium sulfate and requires no separation except substantial removal of particles retained by the Tyler #48 sieve.

The concentration of ammonium sulfate in a suspension of the invention should be between about 30 wt. % and 70 wt. %. It is preferred that the ammonium sulfate concentration be between about 40 wt. %. and 70 wt. % More preferably, the ammonium sulfate concentration should be between about 50 wt. %. and 70 wt. %.

It is desirable to prepare a single product with a combination of a herbicide, ammonium sulfate adjuvant and a fertilizer. The additional particles can be ground with the ammonium sulfate or the suspension can be made and then the additional particles added to the suspension The single non-ionic surfactant in a suspension of the invention is selected from the group consisting of alkyl-phenoxy-poly(ethylenoxide)alkanols, ethoxylated aliphatic $C_{11}$ to $C_{15}$ alcohols, ethylene oxide-propylene oxide block coplymers and ethoxylated fatty acids. For the purposes of this patent, a "single surfactant" is a surfactant that falls within a single chemical genus but may include a mixture of species having molecular weights differing by up to 150 g/mol. Thus, the "single surfactant" specifically includes ethoxylated derivatives having a limited range of carbon atoms and/or ethoxy units. More specifically, the "single surfactant" includes ethoxylated derivatives of partially purified aliphatic alcohols or fatty acids having a limited range of molecular weights.

Preferably, the non-ionic surfactant possesses an average molecular weight from about 300 to about 1000. Surprisingly, and contrary to theory, non-ionic surfactants within this molecular weight range yield more stable suspensions than higher molecular weight surfactants. Preferred alkyl-phenoxy-poly(ethylenoxide)alkanols, include dodecylphenoxy poly(ethylene oxide)$_{9.5-11}$ ethanol[1] of about 713 average molecular weight (MW) available under the tradename Igepal® RC-630, dodecylphenoxy poly(ethylene oxide)$_9$ ethanol of about 643 MW (Igepal® RC-520), octylphenoxy poly(ethylene oxide)$_7$ ethanol of about 514 MW (Igepal® CA-630), octylphenoxy poly(ethylene oxide)$_5$ ethanol of about 426 MW (Igepal® CA-520) and nonylphenoxy poly(ethylene oxide)$_4$ ethanol of about 396 MW (Witconol® NP-40). The Igepal® surfactants are products of Rhodia Inc. The Witconol® is a product of Witco Corporation.

Preferred ethoxylated alcohols include a $C_{12}$-$C_{14}$ secondary aliphatic alcohol (ethoxylate)$_9$ of about 596 average MW (Tergitol® 15-S-9), a $C_{12}$-$C_{14}$ secondary alcohol (ethoxylate)$_{12}$ of about 728 average MW (Tergitol® 15-S-12), and undecanol (ethoxylate)$_9$ about 568 MW (Neodol® 1-9). The Tergitol® surfactants are products of the Union Carbide Division of Dow Chemical. The Neodol® is a product of Shell Chemical. A preferred ethoxylated acid is oleyl (ethoxylate)$_{10}$ of about 708 MW (Brij® 97), a product of Uniqima Corporation.

The most preferred surfactant is dodecylphenoxy poly(ethylene oxide)$_{9.5-11}$ ethanol of about 713 average molecular weight (MW) available under the tradename Igepal® RC-630.

The concentration of the surfactant is between about 1 wt. % and about 9 wt. % in a suspension of the invention. Preferably the surfactant concentration is about 2.5 wt. % to about 6.5 wt. %.

The water-soluble glycol liquids approved for agricultural application are ethylene glycol, diethylene glycol, triethylene glycol, propylene glycol and dipropylene glycol. Preferred in this invention are ethylene glycol and propylene glycol. Most preferred is propylene glycol.

The concentration of the glycol liquid is between about 20 wt. % to about 80 wt. % of the suspension of the invention, preferably, between about 30 wt. % to about 70 wt. %, more preferably between about 30 wt. % to about 60 wt. %, and most preferably, between about 30 wt. % to about 50 wt. %.

Surprisingly, It has been found that incorporation of about 0.03 to 2 wt. % of methylthio-α-hydroxybutyric acid (chemical formula: $CH_3SCH_2CH_2CH(OH)COOH$) further enhances the stability and further reduces the viscosity of the suspensions of the invention. Over one hundred other compounds had been screened for this purpose without success and there appears to be no prior art reference suggesting this functionality for methylthio-α-hydroxybutyric acid. The synthesis of methylthio-α-hydroxybutyric acid has been described in U.S. Pat. No. 2,745,745 hereby incorporated by reference to the extent not incompatible herewith. Methylthio-α-hydroxybutyric acid is an article of commerce sold as an animal feed supplement by Aventis Animal Nutrition, Alpharetta, Ga. in the form of an 88% aqueous solution under the tradename Rhodimet® AT-88.

The suspensions of the invention can be prepared by simple mixing of the ingredients provided that the solid particles have been previously ground to the proper size. The mixing can be done by any of the well known methods for combining solids and liquids such as described in Perry's Chemical Engineers Handbook, Sixth Edition, P. 19.5-19.24, McGraw Hill, N.Y., 1983. In some cases it may be desirable to grind or mill the solids in the glycol liquid but this choice is well known in the art of grinding. Any conventional means of providing uniform mixing is suitable such as pug mills, blenders, agitated tanks, and helical mixers. The order of introduction of the materials appears to not be critical, but usually the surfactant is added last to provide a more uniform distribution of the surfactant.

The suspensions of the invention are characterized by stability and pourability. Experience has shown that suspensions that are stable for several days are stable for periods exceeding six months. Suspension stability was determined by leaving a sample sit undisturbed at room temperature (20-23° C.) for one or more days and measuring the volume of the free liquid that separated by syneresis relative to the volume of the suspension. The suspensions of the invention exhibit a syneresis percentage less than 10 vol. % after 2 days preferably less than 5 vol. % and most preferably less than 1 vol %.

It should be noted that this method of determining syneresis percentage is much more demanding than the method described in U.S. Pat. No. 5,707,551 where the suspension container is tumbled through thirty inversions before measuring any free liquid.

Several days after preparation, suspension samples were also examined for ability to pour. Pourability ratings were determined by the speed and the completeness of flow of a suspension from a tilted beaker. A value of 5 was assigned if the sample had a flow about that of water, a value of 0 if there was no immediate flow indicating a possible Bingham plastic state, and intermediate values between these two extremes. Suspensions of the invention have pourability ratings of 2 or better, preferably 3 or better and most preferably 4 or better.

A quantitative measure of pourability was obtained as follows: The suspension to be characterized was prepared in a total quantity of 15.65 g. After thorough mixing in a beaker, this suspension was transferred quickly (less than 10 seconds) into a glass funnel of 60° cone angle, and having a stem of 4 mm inside diameter and of 60 mm length. The rate at which a suspension was discharged from the funnel stem was measured by means of a scale and recorded vs. time. The approximate relationship between the relative pourability rating and the time required for 90% of the suspension (14.1 g) to discharge through the funnel was as follows:

| 90% Discharge Time, minutes | Pourability Rating |
| --- | --- |
| <5 | 5 |
| 10-15 | 4 |
| 25-30 | 3 |
| 40-50 | 2 |
| >60 | 1 |

Intermediate discharge times were taken to correspond approximately to intermediate pourability ratings. As an example, a discharge time of 20 minutes corresponded approximately to a 3.5 pourability rating.

The following examples are presented to provide a more complete understanding of the invention. The specific techniques, conditions, materials, proportions and reported data set forth to illustrate the principles of the invention are exemplary and should not be construed as limiting the scope of the invention.

EXAMPLE 1

Ammonium sulfate granules of approximately 1 mm average size were obtained from Rhone-Poulenc. The granules were 98 wt. % ammonium sulfate containing less than 0.1 wt. % of water insoluble carbonaceous impurities. Forty pounds of this material were ball milled at the Union Process Company, Akron, Ohio. The ammonium sulfate was charged to a size 1S ball mill together with ¼ inch (6.35 mm) stainless steel balls and batch dry ground at 350 RPM for 55 minutes. Cooling water on the ball mill jacket maintained the batch temperature at about 23° C. At the completion of the ball milling, the ammonium sulfate was screened to remove substantially all particles not passable through a Tyler #48 screen. The particle size distribution of the screened material was as follows in Table I.

TABLE I

| Tyler Sieve No. | Opening size, mm | Wt. % Retained |
| --- | --- | --- |
| 48 | 0.30 | Less than 0.1 |
| 60 | 0.25 | 0.3 |
| 80 | 0.18 | 0.4 |
| 100 | 0.15 | 0.3 |
| 200 | 0.075 | 18 |
| 230 | 0.060 | 49 |

TABLE I-continued

| Tyler Sieve No. | Opening size, mm | Wt. % Retained |
| --- | --- | --- |
| 400 | 0.030 | 19 |
| pan | 0 | 13 |

COMPARATIVE EXAMPLE 2

To determine if satisfactory suspensions of ammonium sulfate can be prepared in a glycol without the presence of a surfactant, the following experiment was performed. Three mixtures of the milled and sieved ammonium sulfate described in Example 1 were prepared with propylene glycol, ethylene glycol and diethylene glycol respectively, each in weight ratios of 61.7/38.3 (w/w)% ammonium sulfate/glycol. No surfactant was added to the mixtures. The glycols had been obtained from Fisher Scientific. The ethylene glycol had a boiling range of 196-199° C. The propylene glycol and diethylene glycol were of 99.5% purity.

After only 24 hours it was obvious that the mixtures were not satisfactory suspensions. The mixture prepared with propylene glycol exhibited some pourability for its top half, however the bottom half of the sample was a thick crumbly-type of solid. The mixture prepared using ethylene glycol had less pourability in its top portion and the residue at the bottom was a little less stiff than the propylene glycol mixture. The mixture prepared with diethylene glycol was very similar to the propylene glycol sample having a thick residue at the bottom of the container.

EXAMPLES 3-5 AND COMPARATIVE EXAMPLES 6-13

The following examples show the effect of single surfactants of different types, non-ionic, anionic and cationic, and of differing molecular weights, on the pourability of ammonium sulfate suspensions. Several portions of the milled and sieved ammonium sulfate described in Example 1 were each thoroughly mixed in a beaker with propylene glycol (Fisher Scientific, 99.5% assay) in proportions of 61.7/38.3 (w/w)% respectively. This was followed by admixing in each portion a single one of the surfactants indicated in Table II below. Ammonium sulfate concentration in the suspension varied slightly from 57.0 to 59.2 wt. % depending on how much surfactant was added to the mixture.

The suspensions were left to stand undisturbed at room temperature after preparation until examination for pourability after 2, 5, and 8 days. The compositions of the suspensions and the pourability ratings are shown in Table II below. The pourability ratings obtained on day 2 were consistent with the pourabilities observed on day 5 and day 8 except for the Adogen® 464S sample. This suspension exhibited some thickening at the bottom of the beaker and its pourability declined with time.

The best pourability was obtained with nonionic surfactants, particularly with the two surfactants having molecular weights around 700 g/mol.

TABLE II

| Example or Comp. Ex. No. | Name of Surfactant | Description of Surfactant | Approx. Avg. Molecular Weight | Wt. % Surfactant | Pourability Rating* |
|---|---|---|---|---|---|
| | | NON-IONICS | | | |
| 3 | Igepal RC-630 | Dodecylphenoxy poly(ethylene oxide)$_{9.5-11}$ ethanol | 713 | 5.7 | 4 |
| 4 | Tergitol ® 15-S-12 | $C_{12}$-$C_{14}$ secondary alcohol (ethoxylate)$_{12}$ | 728 | 7.5 | 4 |
| 5 | Synperonic ® PE/L61 | Ethylene oxide/propylene oxide block copolymer | 2100 | 4.1 | 3 |
| 6 (Comp.) | Tween ® 85 | Poly(ethylene oxide)$_{20}$ sorbitan trioleate | 1838 | 4.5 | 1 |
| 7 (Comp.) | Atlox ® 4912 | 12-hydrostearic acid (propoxylate) | 4900 | 4.3 | 1 |
| 8 (Comp.) | Pergosperse ® 400DO | Polyethylene glycol(400)dioleate | 932 | 5.3 | 1 |
| 9 (Comp.) | Zephrym ® PD2206 | Polymeric ester | 5000 | 5.0 | 1 |
| | | ANIONICS | | | |
| 10 (Comp.) | Rhodameen ® PN-430 | Poly(oxyethylated)$_5$ tallow amine | 477 | 4.5 | 1 |
| 11 (Comp.) | Mazeen ® DBA 1 Amine | 2-(dibutylamino)amine | 161 | 4.8 | 1 |
| 12 (Comp.) | Foamphos ® NP-3 | Nonoxynol-3 phosphate | 696 | 4.1 | 1 |
| | | CATIONIC | | | |
| 13 (Comp.) | Adogen ® 464S | Methyl ltri $C_8$-$C_{10}$ quaternary ammonium chloride | 445 | 4.1 | 3 |

*5 = water-like
0 = did not flow immediately (possible Bingham plastic state)

EXAMPLES 14-24

The following examples show the effects on the stability and pourability of ammonium sulfate suspensions of several non-ionic surfactants having molecular weights in the range of about 396 to about 2400.

Several portions of the milled and sieved ammonium sulfate described in Example 1 were each thoroughly mixed with propylene glycol (Fisher Scientific, 99.5% assay) and surfactant in a beaker. Ammonium sulfate, propylene glycol and surfactant concentrations were 58.9 wt. %, 36.6 wt. % and 4.5 wt. % respectively with one exception. The exception was the suspension containing Tegitol® 15-S-12 which had ammonium sulfate, propylene glycol and surfactant concentrations of 59.3 wt. %, 36.9 wt. % and 3.8 wt. % respectively.

The suspensions were left undisturbed for two days at room temperature after preparation. The compositions of the suspensions the syneresis and pourability observations after two days are shown in Table IIII.

The best combination of stability (zero syneresis) and very good pourability was obtained with dodecylphenoxy poly(ethyleneoxide)$_{9.5-11}$ ethanol (about 713 MW) obtained commercially as Igepal® RC-630, with dodecylphenoxy poly(ethylene oxide)$_9$ ethanol (about 653 MW) obtained commercially as Igepal® RC-520, with tridecyl alcohol (ethoxylate)$_6$ (about 464 MW) obtained commercially as Witconol® TD-60, and with nonylphenol (ethoxylate)$_4$ obtained commercially as Witconol® NP-40.

TABLE III

| Ex. or Comp. Ex. No | Name of Surfactant | Description of Surfactant | Approx. Avg. Molecular Weight | Vol. % Syneresis | Pourability Rating* |
|---|---|---|---|---|---|
| 14 | Igepal ® RC-630 | dodecylphenoxy poly(ethyleneoxide)$_{9.5-11}$ ethanol | 713 | 0 | 4 |
| 15 | Igepal ® RG-520 | Dodecylphenoxy poly(ethylene oxide)$_9$ ethanol | 653 | 0 | 4 |
| 16 | Igepal ® CA-630 | Dodecylphenoxy poly(ethylene oxide)$_7$ ethanol | 514 | 5.2 | 4 |
| 17 | Igepal ® CA-520 | Dodecylphenoxy poly(ethylene oxide)$_7$ ethanol | 426 | 1.8 | 4 |
| 18 | Tergitol ® 15-S-12 | $C_{12}$-$C_{14}$ secondary alcohol (ethoxylate)$_{12}$ | 728 | 1.8 | 3 |
| 19 | Tergitol ® 15-S-9 | $C_{12}$-$C_{14}$ secondary alcohol (ethoxylate)$_9$ | 596 | 4.4 | 3 |
| 20 | Witconol ® TD-60 | Tridecyl alcohol (ethoxylate)$_6$ | 464 | 0 | 4 |
| 21 | Witconol ® NP-40 | Nonylphenol (ethoxylate)$_4$ | 396 | 0 | 4 |
| 22 | Neodol ® 1-9 | $C_{11}$ alcohol (ethoxylate)$_9$ | 568 | 1.8 | 4 |
| 23 | Neodol ® 25-7 | $C_{12-15}$ alcohol (ethoxylate)$_{7-8}$ | 537 | 0 | 4 |
| 24 | Brij ® 97 | poly(ethylene oxide)$_{10}$ oleyl ether | 708 | 0 | 4 |

*5 = water-like
0 = did not flow immediately (possible Bingham plastic state)

EXAMPLES 25-36

Mixtures were prepared having the proportions shown in Table IV below consisting of the milled and sieved ammonium sulfate described in Example 1, propylene glycol (Fisher Scientific. 99.5% assay) and dodecylphenoxy poly (ethyleneoxide)$_{9.5-11}$ ethanol (Igepal® RC-630) surfactant. The suspensions were left undisturbed for two days at room temperature after preparation with thorough mixing. The syneresis percentage, pourability and viscosity observations after two days are shown in Table IV. The free liquid remained unchanged for each suspension after four days.

The apparent viscosities of the suspensions were measured using a Brookfield DV-E viscometer with an LV-4 spindle at 2.5 rpm after stabilizing for 5 minutes. The LV-4 spindle is a straight cylinder having a diameter of 3.15 mm.

TABLE IV

| Ex. No. | Wt. % ammonium sulfate | Wt. % propylene glycol | Wt. % Igepal ® RC-630 | Vol. % Syneresis, | Pourability Rating | Apparent Viscosity, poise |
|---|---|---|---|---|---|---|
| 25 | 61.7 | 35.0 | 3.3 | 0 | 3 | 9360 |
| 26 | 61.5 | 34.9 | 3.6 | 0 | 3 | 9120 |
| 27 | 61.3 | 34.7 | 4.0 | 0 | 3 | 8880 |
| 28 | 61.1 | 34.6 | 4.3 | 0 | 3 | 7680 |
| 29 | 60.9 | 34.5 | 4.6 | 0 | 3.5 | 19400 |
| 30 | 60.7 | 34.4 | 4.9 | 0 | 3.5 | 13000 |
| 31 | 60.5 | 34.3 | 5.2 | 0 | 3.5 | 11000 |
| 32 | 60.3 | 34.2 | 5.5 | 0 | 3 | 9840 |
| 33 | 58.5 | 36.4 | 5.1 | 0 | 3.5 | 11040 |

TABLE IV-continued

| Ex. No. | Wt. % ammonium sulfate | Wt. % propylene glycol | Wt. % Igepal® RC-630 | Vol. % Syneresis | Pourability Rating | Apparent Viscosity, poise |
|---|---|---|---|---|---|---|
| 34 | 55.9 | 39.3 | 4.8 | <1 | 3.5 | 5760 |
| 35 | 58.4 | 36.3 | 5.4 | <1 | 3 | 9840 |
| 36 | 55.7 | 39.2 | 5.1 | <1 | 3 | 5520 |

Each of these suspensions of the invention showed excellent stability, good pourability and moderate viscosity.

EXAMPLES 37-41

Mixtures were prepared ammonium sulfate, Igepal® RC-630 (dodecylphenoxy poly(ethyleneoxide)$_{9.5-11}$ ethanol) surfactant and either ethylene glycol or propylene glycol. The ammonium sulfate was the milled and sieved ammonium sulfate described in Example 1. The ethylene glycol and propylene glycol were as described in Comparative Example 2. The resulting suspensions had the proportions shown in Table V below. The suspensions were left undisturbed for four days at room temperature after preparation with thorough mixing. The free liquid, and pourability after four days were measured and are shown in Table V.

TABLE V

| Ex. No. | Glycol | Wt. % ammonium sulfate | Wt. % Glycol | Wt. % Igepal® RC-630 | Vol. % Syneresis | Pourability Rating |
|---|---|---|---|---|---|---|
| 37 | ethylene | 59.3 | 36.9 | 3.8 | 0 | 3 |
| 38 | ethylene | 60.9 | 34.5 | 4.6 | <1 | 2 |
| 40 | propylene | 59.3 | 36.9 | 3.8 | 0 | 4 |
| 41 | propylene | 58.9 | 36.6 | 4.5 | 0 | 4 |

Each of these suspensions of the invention showed excellent stability and fair to very good pourability.

EXAMPLE 42-43

Two suspensions of the invention were prepared having compositions of 59.1 wt. % ammonium sulfate, 4.2 wt. % dodecylphenoxy poly(ethylene oxide)$_{9.5-11}$ ethanol (Igepal® RC-630) and 36.7 wt. % glycol liquid. The glycol was ethylene glycol in one suspension and propylene glycol in the other. The ammonium sulfate was the milled and sieved material described in Example 1. The ethylene glycol and propylene glycols were the same materials described in Comparative Example 2.

15.65 g of each suspension was transferred quickly (less than 10 seconds) into a glass funnel of 60° cone angle, and having a stem of 4 mm inside diameter and of 60 mm length. The rate at which a suspension was discharged from the funnel stem was measured by means of a scale and recorded vs. time. The measurements are shown in Table VI and are plotted as fractional discharge (culmulative discharge/15.65) vs time in FIG. 1. The pourability ratings were 3 for the suspension in ethylene glycol and 4 for the suspension in propylene glycol.

TABLE VI

| Example 42 Ammonium Sulfate Suspension In Ethylene Glycol | | Example 43 Ammonium Sulfate Suspension In Propylene Glycol | |
|---|---|---|---|
| Time, min | Cumulative Discharge, g | Time, min | Cumulative Discharge, g |
| 1 | 0.79 | 2 | 2.70 |
| 3 | 2.01 | 3 | 4.00 |
| 5 | 3.1 | 4 | 5.50 |
| 7 | 4.26 | 5 | 6.70 |
| 9 | 5.38 | 6 | 8.00 |
| 11 | 6.65 | 7 | 9.30 |
| 13 | 7.69 | 8 | 10.60 |
| 15 | 8.83 | 9 | 11.70 |
| 17 | 9.91 | 10 | 12.70 |
| 19 | 10.99 | 11 | 13.60 |
| 21 | 11.96 | 12 | 14.20 |
| 23 | 12.49 | 13 | 14.20 |
| 25 | 13.87 | | |
| 27 | 14.3 | | |
| 29 | 14.3 | | |

EXAMPLES 44-45

Two suspensions of the invention were prepared having compositions of 59.1 wt. % ammonium sulfate, 4.2 wt. % dodecylphenoxy poly(ethylene oxide)$_{9.5-11}$ ethanol (Igepal® RC-630) and 36.7 wt. % glycol liquid. The glycol was ethylene glycol in one suspension and propylene glycol in the other. The ammonium sulfate was the milled and sieved material described in Example 1. The ethylene glycol and propylene glycols were the same materials described in Comparative Example 2.

To test the rapidity of their dispersion and dissolution in water, 1 ml of each suspension was injected from a syringe into 150 ml of tap water in a 250 ml beaker. The water was stirred by a magnetic stir bar of 37 mm×9 mm dimensions rotating at about 200 RPM. As the suspensions were injected into the water, they dispersed within about one second. The time to dissolve was measured from the point of injection to the point where solid particles could no longer be observed. The results were as follows:

TABLE VII

| Ex. No. | Glycol in Suspension | Dissolving Time, sec |
|---|---|---|
| 44 | ethylene glycol | 37 |
| 45 | propylene glycol | 24 |

EXAMPLES 46-47

The following examples illustrate suspensions of the invention containing either a herbicide or a fertilizer. The ammonium sulfate was the milled and sieved material described in Example 1. The ethylene glycol was the same material described in Comparative Example 2.

The other agricultural solids were RoundUp®DryPak herbicide and diammonium phosphate $(NH_4)_2HPO_4$. RoundUp®DryPak herbicid, manufactured by Monsanto Co, is the isopropylamine salt of N-(phosphonomethyl) glycine. It is a member of the class of herbicides known as glyphosates. The diammonium phosphate was obtained from Fisher Scientific.

The RoundUp®DryPak and the diammonium phosphate were separately ground in a small (~30 ml) SPEX Model 8000 Mixer/Mill using two ½ inch (1.27 cm) diameter stainless steel balls. The ground solids were screened through a Tyler # 48 sieve. Particles retained on the Tyler #48 sieve were discarded. A typical particle size distribution for the ground and sieved solids is listed in Table VIII.

TABLE VIII

| Tyler Sieve No. | Weight % Retained on Sieve |
| --- | --- |
| 48 | 0 |
| 60 | 6 |
| 80 | 15 |
| 100 | 31 |
| 200 | 13 |
| 400 | 19 |
| pan | 16 |

Suspensions of the invention were prepared each containing 59.1 wt. % total agricultural solids, 36.7 wt. % ethylene glycol and 4.2 wt. % of dodecylphenoxy poly(ethylene oxide)$_{9.5-11}$ ethanol (Igepal® RC-630) surfactant. The suspensions, their percent syneresis, and pourability ratings after 2 days of undisturbed storage at room temperature are shown in Table IX.

TABLE IX

| Ex. No. | Solids Composition | Vol. % Syneresis | Pourability Rating |
| --- | --- | --- | --- |
| 46 | isopropylamine salt of N-(phosphonomethyl) glycine | 0 | 3 |
| 47 | $(NH_4)_2SO_4/(NH_4)_2HPO_4$ – 67/33 (w/w) % | 0 | 4 |

EXAMPLES 48-50

Three suspensions were prepared consisting of 59.1 wt. % of the milled and sieved ammonium sulfate described in Example 1, 36.7 wt. % propylene glycol (Fisher Scientific, 99.5% assay) and 4.2 wt. % dodecylphenoxy poly(ethylene oxide)$_{9.5-11}$ ethanol (Igepal® RC-630) surfactant.

One of these suspensions was mixed with 0.3 wt. % of methylthio-α-hydroxybutyric acid (chemical formula: $CH_3SCH_2CH_2CH(OH)COOH$). The methylthio-α-hydroxybutyric acid was purchased from Aventis Animal Nutrition, Alpharetta, Ga. in the form of an 88% aqueous solution under the tradename Rhodimet® AT-88. A second one of these suspensions was mixed with 0.6 wt. % methylthio-α-hydroxybutyric acid. The third suspension was left unchanged as a control The suspensions were left undisturbed for six days at room temperature after preparation. The syneresis percentage, and pourability rating after six days are shown in Table X.

TABLE X

| Ex. No. | Wt. % methylthio-α-hydroxybutyric acid | Vol. % Syneresis | Pourability Rating |
| --- | --- | --- | --- |
| 48 | 0 | 0 | 3 |
| 49 | 0.3 | 0 | 4 |
| 50 | 0.6 | 0 | 4 |

EXAMPLE 51

A suspension of the invention is prepared containing 59.1 wt. % ammonium sulfate, 36.7 wt. % propylene glycol, and 4.2 wt. % dodecylphenoxy poly(ethylene oxide)$_{9.5-11}$ ethanol (Igepal® RC-630). The ammonium sulfate is the milled and sieved material described in Example 1. The propylene glycol is the same as described in Comparative Example 2.

The suspension is dispersed and mixed in sufficient water to bring the ammonium sulfate concentration down to 1 wt. %. Added to this mixture is 1 wt. % of Monsanto Rodeo® brand glyphosate herbicide (isopropylamine salt of N-(phosphonomethyl)glycine) to form a herbicide/adjuvant spray solution.

Weed species grown in small pots are sprayed with this solution at the rate of about 6 gallons per acre. This corresponds to a doseage of about 0.5 lbs/acre of glyphosate and 0.5 lb/acre of ammonium sulfate adjuvant. The weed species sprayed are Velvet Leaf, Morning Glory, and Johnson Grass, known as difficult-to-kill weeds. As a control, another group of the same weeds is sprayed with a solution containing only glyphosate at a doseage of 0.5 lb acre.

Fourteen days after the treatment the plants are cut off at ground leveled and weighed. It is found that the new growth of the weeds sprayed with the herbicide/adjuvant solution made from the suspension of the invention is significantly less than the new growth of weeds sprayed with the glyphosate solution.

What is claimed is:

1. A stable agricultural solids suspension readily dispersible in water, the suspension comprising:
   a. agricultural solids comprising at least one of a fertilizer, a herbicide, and a pesticide, and combinations thereof, said agricultural solids having particles at least 99 wt. % passable through a Tyler #48 sieve;
   b. a single non-ionic surfactant selected from the group consisting of alkyl-phenoxy-poly(ethylenoxide)alkanols, ethoxylated aliphatic $C_{11}$ to $C_{15}$ alcohols, ethylene oxide-propylene oxide block copolymers and ethoxylated fatty acids;
   c. a water-soluble glycol liquid consisting of at least one member selected from the group consisting of ethylene glycol, and propylene glycol; and
   d. methylthio-α-hydroxybutyric acid.

2. The agricultural solids suspension of claim 1, wherein the concentration of the agricultural solids is between about 20 wt. % and 80 wt. %; the concentration of the glycol liquid is between about 20 wt. % and about 80 wt. %; and the concentration of the non-ionic surfactant is between about 1 wt. % and about 9 wt. %.

3. The agricultural solids suspension of claim 1, wherein the concentration of the agricultural solids is between about 50 wt. % and about 70 wt. %; the concentration of the glycol liquid is between about 30 wt. % and about 50 wt. %; and the concentration of the non-ionic surfactant is between about 2.5 wt. % and 6.5 wt. %.

4. The agricultural solids suspension of claim 1, wherein the agricultural solids comprise at least one member selected from the group consisting of ammonium sulfate (($NH_4)_2SO_4$), diammonium phosphate (($NH_4)_2HPO_4$) and the isopropylamine salt of N-(phosphonomethyl) glycine.

5. The agricultural solids suspension of claim 1, wherein the molecular weight of the non-ionic surfactant is between about 300 and 1000.

6. The agricultural solids suspension of claim 1, wherein the non-ionic surfactant is selected from the group consisting of dodecylphenoxy poly(ethylene oxide)$_{9.5-11}$ ethanol, dodecylphenoxy poly(ethylene oxide)$_9$ ethanol, octylphenoxy poly(ethylene oxide)$_7$ ethanol, octylphenoxy poly(ethylene oxide)$_5$ ethanol, and nonylphenoxy poly(ethylene oxide)$_4$.

7. The agricultural solids suspension of claim 1, wherein the non-ionic surfactant is selected from the group consisting of a $C_{12}$-$C_{14}$ secondary aliphatic alcohol (ethoxylate)$_9$, a $C_{12}$-$C_{14}$ secondary alcohol (ethoxylate)$_{12}$, undecanol (ethoxylate)$_9$ and oleyl (ethoxylate)$_{10}$.

8. The agricultural solids suspension of claim 1, wherein the non-ionic surfactant is dodecylphenoxy poly(ethylene oxide)$_{9.5-11}$ ethanol.

9. The agricultural solids suspension of claim 1, wherein the glycol liquid is propylene glycol.

10. The stable agricultural solids suspension of claim 1 further comprising an adjuvant.

11. A stable suspension of ammonium sulfate (($NH_4$)$_2SO_4$) readily dispersible in water, the suspension comprising:
 a. ammonium sulfate particles at least 99 wt. % passable through a Tyler #48 sieve;
 b. a single non-ionic surfactant selected from the group consisting of alkyl-phenoxy-poly(ethylenoxide)alkanols, ethoxylated aliphatic $C_{11}$ to $C_{15}$ alcohols, ethylene oxide-propylene oxide block copolymers and ethoxylated fatty acids;
 c. a water-soluble glycol liquid consisting of at least one member selected from the group consisting of ethylene glycol, and propylene glycol; and
 d. methylthio-α-hydroxybutyric acid.

12. The ammonium sulfate suspension of claim 11, wherein the concentration of the agricultural solids is between about 30 wt. % and 70 wt. %; the concentration of the glycol liquid is between about 30 wt. % and about 70 wt. %; and the concentration of the non-ionic surfactant is between about 1 wt. % and about 9 wt. %.

13. The ammonium sulfate suspension of claim 11, wherein the concentration of the ammonium sulfate is between about 40 wt. % and 70 wt. %; the concentration of the glycol liquid is between about 30 wt. % and about 60 wt. %; and the concentration of the non-ionic surfactant is between about 1 wt. % and about 9 wt. %.

14. The ammonium sulfate suspension of claim 11, wherein the concentration of the ammonium sulfate is between about 50 wt. % and about 70 wt. %; the concentration of the glycol liquid is between about 30 wt. % and about 50 wt. %; and the concentration of the non-ionic surfactant is between about 2.5 wt. % and 6.5 wt. %.

15. The ammonium sulfate suspension of claim 11, wherein the non-ionic surfactant has a molecular weight between about 300 and about 1000.

16. The ammonium sulfate suspension of claim 11, wherein the non-ionic surfactant is selected from the group consisting of dodecylphenoxy poly(ethylene oxide)$_{9.5-11}$ ethanol, dodecylphenoxy poly(ethylene oxide)$_9$ ethanol, octyiphenoxy poly(ethylene oxide)$_7$ ethanol, octylphenoxy poly(ethylene oxide)$_5$ ethanol, and nonylphenoxy poly(ethylene oxide)$_4$.

17. The agricultural solids suspension of claim 11, wherein the non-ionic surfactant is selected from the group consisting of a $C_{12}$-$C_{14}$ secondary aliphatic alcohol (ethoxylate)$_9$, a $C_{12}$-$C_{14}$ secondary alcohol (ethoxylate)$_{12}$, undecanol (ethoxylate)$_9$ and oleyl (ethoxylate)$_{10}$.

18. The ammonium sulfate suspension of claim 11, wherein the non-ionic surfactant is is dodecylphenoxy poly (ethylene oxide)$_{9.5-11}$ ethanol.

19. The ammonium sulfate suspension of claim 11, wherein the glycol liquid is propylene glycol.

20. The stable suspension of claim 11 further comprising an adjuvant.

\* \* \* \* \*